US00PP22856P3

(12) United States Plant Patent
Carruth et al.

(10) Patent No.: US PP22,856 P3
(45) Date of Patent: Jul. 17, 2012

(54) SHRUB ROSE PLANT NAMED 'WEKPHORN'

(50) Latin Name: *Rosa hybrida*
Varietal Denomination: WEKphorn

(75) Inventors: Thomas F. Carruth, Altadena, CA (US); Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/807,485

(22) Filed: Sep. 7, 2010

(65) Prior Publication Data

US 2012/0060245 P1 Mar. 8, 2012

(51) Int. Cl.
*A01H 5/00* (2006.01)

(52) U.S. Cl. ..... Plt./107

(58) Field of Classification Search ..... Plt./107
See application file for complete search history.

*Primary Examiner* — Susan McCormick Ewoldt
(74) *Attorney, Agent, or Firm* — McKee, Voorhees & Sease, P.L.C.

(57) ABSTRACT

A new variety of shrub rose suitable for garden decoration, having flowers of velvety warm pink coloration.

1 Drawing Sheet

Classification: The present invention relates to a new *Rosa hybrida* plant.

Variety denomination: The new plant has the varietal denomination 'WEKphorn'.

BACKGROUND OF THE INVENTION

This invention relates to a new and distinct variety of Shrub Rose. It was discovered outside in a cultivated field during the summer of 2007 in Wasco, Calif. as a whole plant natural occurring mutation of the variety known as 'WEKcisbako' (U.S. Plant Pat. No. 18,552).

SUMMARY OF THE INVENTION

Among the features which distinguish the new variety from other presently available and commercial rose cultivars known to the inventor are the following combination of characteristics: its high degree of resistance to black spot and powdery mildew, its many stipitate glands on surface of the bud and the peduncle, its several stipitate glands on the new shoots and its velvety warm pink coloration that lasts throughout the life of the flower. The plant has a bushy moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKphorn' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from the cultivar of origination, 'WEKcisbako' by the following combination of characteristics: whereas 'WEKphorn' bears flowers of velvety warm pink coloration, the cultivar of origination bears flowers of flame red coloration.

COMPARISON WITH THE CLOSEST COMMERCIALLY AVAILABLE CULTIVAR

The closest commercially available cultivar to the new variety is the cultivar of origination 'WEKcisbako'.

BRIEF DESCRIPTION OF ILLUSTRATION

The accompanying photograph illustrates the new variety from 3-4 year old rose plants of the new variety grown outdoors in Pomona, Calif. in the month of August and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of August. Phenotypic expression may vary with environmental, cultural and climatic conditions, as well as differences in conditions of light and soil.

FLOWER

The new variety sometimes bears its flowers singly, usually in clusters of two to six or more per stem. Flowers may be borne in somewhat regular rounded clusters on strong medium stems (about 19 to about 58 cm.). Outdoors, the plant blooms abundantly and nearly continuously during the growing season. The flowers have a slight tea fragrance.

BUD

The peduncle is about 1.2 to about 3.5 cm. in length, of average caliper (about 0.2 to about 0.3 cm. in diameter), and usually erect. It is rough with many stipitate glands. Peduncle color is between 146C and 146A sometimes lightly suffused, especially on the side exposed to the sun, with between 187B and 183B.

Before the calyx breaks, the bud is about 0.7 to about 1.1 cm. in diameter at the widest point, about 1.2 to about 1.7 cm. in length, and very pointed in shape. The surface of the bud bears some foliaceous appendages and many stipitate glands, usually with slender entire foliaceous parts extending beyond the tip of the bud about ¼ or more of its length. Bud color is between 146B and 137B sometimes lightly suffused, especially on the side exposed to the sun, with between 187B and 183B.

The sepals are about 1.9 to about 3.4 cm. in length and about 0.6 to about 0.8 cm. in width at the widest point. The outer surface color of the sepal is between 146B and 137B sometimes lightly suffused, especially on the side exposed to the sun, with between 187B and 183B. The very tip of the sepal is usually moderately suffused with between 187B and 183B. The inner surface color of the sepal is between 137B and 138B and covered with fine wooly tomentum; sepal margins are lined with some stipitate glands and hairs.

The receptacle of the flower is moderately short in length (about 0.4 to about 0.8 cm.) and somewhat thin in caliper (about 0.4 to about 0.7 cm. in diameter). The receptacle is moderately ovoid to somewhat rounded in form. Its surface is moderately smooth with some stipitate glands at the base and with somewhat thin fleshy walls. The receptacle color is between 146B and 137B.

As the petals open (after the calyx breaks), the bud is about 1.1 to about 1.5 cm. in diameter at the widest point, about 1.5 to about 2.6 cm. in length, and pointed to moderately ovoid in form. The color of the under surfaces of the newly opened petals is between 60A and 57A. At the point where the petal attaches, there is a small zone of between 8C and 10C. The color at the base of the upper surfaces of the newly opened petals is near 53B gradually suffusing toward the edge of the petals with between 53A and 57A. At the point where the petal attaches, there is a small zone of between 12A and 13B.

BLOOM

When fully open, the bloom ranges from about 6.3 to about 9.1 cm. in diameter. Petalage is single with 5 petals and no petaloids. When partially open, the bloom form is cupped, and the petals are loosely cupped with petal edges moderately reflexed outward. When fully open, the bloom form is moderately cupped to somewhat flat, and the petals are more loosely cupped to slightly undulated with petal edges moderately reflexed outward.

PETALS

The substance of the petals is moderately heavy and of somewhat thin thickness, with upper surfaces moderately satiny and under surfaces matte. The petals are about 3.0 to about 4.1 cm. in length and about 2.4 to about 3.9 cm. in width at the widest point. Petal margins are entire.

The petals are broadly obovate in shape with rounded apices and sometimes slightly notched with one notch.

Petaloids are absent from the flower.

NEWLY OPENED FLOWER

The under surface color of the petals is between 58B and 57B. At the point where the petal attaches, there is a moderately small zone of between 8D and 11D. The upper surface color of the petals is between 57A and 57B. At the point where the petal attaches, there is a moderately small zone of between 12B and 13C.

The general tonality of the newly opened flower is between 57A and 57B.

THREE-DAY-OLD FLOWER

The under surface color of the petals is between 61C and 57B. At the point where the petal attaches, there is a moderately small zone of between 155B and 155D. The upper surface color of the petals is between 66A and 66B. At the point where the petal attaches, there is a moderately small zone of between 155B and 155D.

The general tonality of the three-day-old flower is between 66A and 66B.

On the spent bloom, the petals usually drop off cleanly.

In August in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 95) and are arranged regularly about the pistils. The filaments are of medium length (about 0.4 to about 0.9 cm.) most with anthers. Filaments are between 6C and 7C at the base suffusing to near 22B in color. The anthers are somewhat small for the class and all open approximately at the same time. Anther color is between 22B and 187C when immature and between 163D and 200B at maturity. Pollen is moderately abundant and near 22C in color.

FEMALE REPRODUCTIVE ORGANS

Pistils vary in number (average about 25). The styles are even, moderately short in length (about 0.3 to about 0.6 cm.), average in caliper and moderately bunched. Stigma color is between 18B and 20C. Style color is near 4D usually heavily suffused with between 53B and 53C. Ovaries are all enclosed in the calyx.

Hips have not been observed on this variety when grown in Pomona, Calif.

FOLIAGE

The compound leaves are usually comprised of three to five leaflets and are borne abundantly. The five-leaflet leaves are about 11.6 to about 14.1 cm. in length and about 9.5 to about 11.4 cm. in width at the widest point, moderately leathery to somewhat crisp in texture, and glossy in finish. The terminal leaflets are about 4.8 to about 6.9 cm. in length and about 3.2 to about 4.9 cm. in width at the widest point, shaped obovate to somewhat oval with acuminate apices and rounded bases. Their margins are usually simply serrate.

The upper surface color of the mature leaf is between 137A and 147A. The under surface color of the mature leaf is between 147B and 147C. The upper surface color of the young leaf is between 146A and 146B, usually moderately suffused with between 187B and 183A. The under surface color of the young leaf is between 147B and 146B, usually heavily suffused with between 187B and 183A.

The rachis is average in caliper and rough. The upper side is shallowly grooved with some hairs and stipitate glands on the edges of the grooves. The under side of the rachis is rough with some stipitate glands and few small prickles. The rachis color is between 146B and 146D sometimes lightly suffused with between 187B and 183A.

The stipules are about 1.2 to about 1.9 cm. in length and of medium width (about 0.4 to about 0.6 cm.) with moderately long straight points that usually turn out at an angle of more than 45 degrees. The stipules color is between 137A and 146C sometimes lightly suffused with between 187B and 183A.

The petiole is average in caliper and rough. The upper side is shallowly grooved with some hairs and stipitate glands on the edges of the grooves. The under side of the petiole is rough with some stipitate glands and few small prickles. The petiole is about 1.4 to about 2.1 cm. in length and about 0.15 to about 0.2 cm in diameter at the widest point. The petiole color is between 146B and 146D sometimes lightly suffused with between 187B and 183A.

The plant displays a high degree of resistance to black spot and powdery mildew and an average degree of resistance to downy mildew and rust as compared to other commercial varieties grown under comparable conditions in Pomona, Calif. The plant's winter hardiness and drought/heat tolerance are yet to be determined.

GROWTH

The plant has a bushy moderately spreading medium height growth habit (about 90 to about 112 cm. in height and about 56 to about 70 cm. spread at the widest point), with very full branching. It displays vigorous growth and the canes are of medium caliper for the class (about 1.2 to about 1.8 cm. in width at the widest point).

The color of the major stems is between 146A and 147B. They bear many large prickles that are about 0.6 to about 0.8 cm. in length. The large prickles are angled moderately downward to slightly hooked with a medium length somewhat broad oval base; prickle color is between 164C and 166A. The major stem bears many small prickles of similar shape and coloration.

The color of the branches is between 146B and 146A. They bear many large prickles which are of similar size and shape to the large prickles on the major stems; prickle color is between 146D and 147C often moderately suffused with between 187B and 183A. The branches bear some small prickles of similar shape and coloration.

The color of the new shoots is between 146B and 146A sometimes lightly suffused with between 187B and 183A. They bear many large prickles which are of similar size and shape to the large prickles on the major stems; prickle color is between 146D and 147C often moderately suffused with between 187C and 183C. The shoots bear several stipitate glands and several small prickles of similar shape and coloration to the large prickles.

We claim:

1. A new and distinct shrub rose plant of the variety substantially as described and illustrated herein.

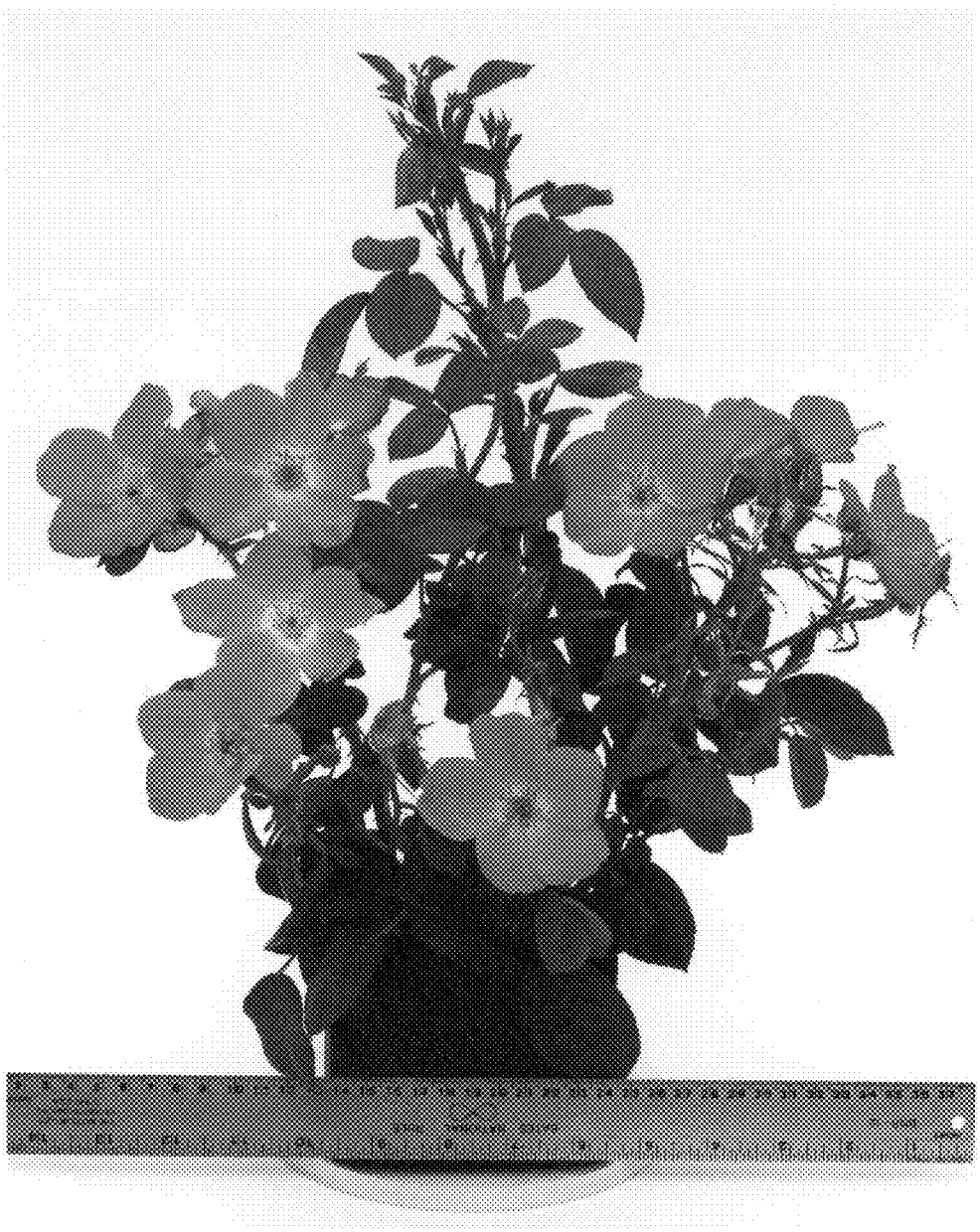

* * * * *